(12) United States Patent
Hirose et al.

(10) Patent No.: US 12,133,684 B2
(45) Date of Patent: Nov. 5, 2024

(54) OPHTHALMIC IMAGING APPARATUS, CONTROLLING METHOD OF THE SAME, AND RECORDING MEDIUM

(71) Applicant: Topcon Corporation, Tokyo (JP)

(72) Inventors: Ryoichi Hirose, Tokyo (JP); Toshihiro Mino, Warabi (JP); Tatsuo Yamaguchi, Warabi (JP)

(73) Assignee: TOPCON CORPORATION, Tokyo (JP)

(*) Notice: Subject to any disclaimer, the term of this patent is extended or adjusted under 35 U.S.C. 154(b) by 748 days.

(21) Appl. No.: 17/211,932

(22) Filed: Mar. 25, 2021

(65) Prior Publication Data

US 2021/0204809 A1   Jul. 8, 2021

Related U.S. Application Data

(63) Continuation of application No. PCT/JP2019/031209, filed on Aug. 7, 2019.

(30) Foreign Application Priority Data

Sep. 28, 2018 (JP) .................. 2018-184102

(51) Int. Cl.
*A61B 3/10* (2006.01)
*A61B 3/12* (2006.01)

(52) U.S. Cl.
CPC ................ *A61B 3/102* (2013.01); *A61B 3/12* (2013.01)

(58) Field of Classification Search
CPC .... A61B 3/00; A61B 3/10; A61B 3/12; A61B 3/14; A61B 3/102; A61B 3/103;
(Continued)

(56) References Cited

U.S. PATENT DOCUMENTS

2013/0301008 A1   11/2013   Srivastava et al.
2016/0317016 A1   11/2016   Oishi
(Continued)

FOREIGN PATENT DOCUMENTS

JP   2009-183332 A   8/2009
JP   2015-515894 A   6/2015
(Continued)

OTHER PUBLICATIONS

English translation of JP 2017217145. (Year: 2017).*
(Continued)

*Primary Examiner* — Jie Lei
(74) *Attorney, Agent, or Firm* — XSENSUS LLP

(57) ABSTRACT

The ophthalmic imaging apparatus (1) of an embodiment example performs motion contrast imaging by applying OCT scanning to an eye (E). The data acquiring unit (2, 100) acquires a plurality of pieces of time-course data respectively corresponding to a plurality of scan points, by conducting repetitive A-scan application to individual scan points. The image constructing unit (220) constructs a motion contrast image from the plurality of pieces of time-course data acquired. The controller (211) controls the data acquiring unit such that data acquisition time intervals of first time-course data corresponding to a first scan point of the plurality of scan points and data acquisition time intervals of second time-course data corresponding to a second scan point become substantially equal to each other.

12 Claims, 5 Drawing Sheets

(58) Field of Classification Search
CPC ... A61B 3/1241; A61B 3/1233; A61B 3/0025; A61B 3/0041; A61B 3/0066; A61B 3/0091; A61B 3/0058; A61B 3/117; A61B 3/1173
USPC ........ 351/206, 205, 208, 210–212, 221, 246
See application file for complete search history.

(56) References Cited

U.S. PATENT DOCUMENTS

| | | | |
|---|---|---|---|
| 2016/0317029 A1 | 11/2016 | Srivastava et al. | |
| 2017/0065171 A1 | 3/2017 | Satake et al. | |
| 2019/0380588 A1 | 12/2019 | Takeno et al. | |

FOREIGN PATENT DOCUMENTS

| | | |
|---|---|---|
| JP | 2016-209200 A | 12/2016 |
| JP | 2017-047113 A | 3/2017 |
| JP | 2017-217145 A | 12/2017 |
| JP | 2018-68578 A | 5/2018 |
| WO | 2017/119437 A1 | 7/2017 |

OTHER PUBLICATIONS

Office Action issued on Jun. 20, 2023, in corresponding Japanese patent Application No. 2022-168295, 10 pages.
Japanese Office Action issued Aug. 2, 2022, in corresponding Japanese Patent Application No. 2018-184102, 9 pp.
Office Action issued on May 10, 2022, in corresponding Japanese patent Application No. 2018-184102, 6 pages.
Extended European search report issued on May 18, 2022, in corresponding European patent Application No. 19866470.8, 7 pages.
International Search Report and Written Opinion mailed on Oct. 21, 2019, received for PCT Application PCT/JP2019/031209, Filed on Aug. 7, 2019, 7 pages including English Translation.

* cited by examiner

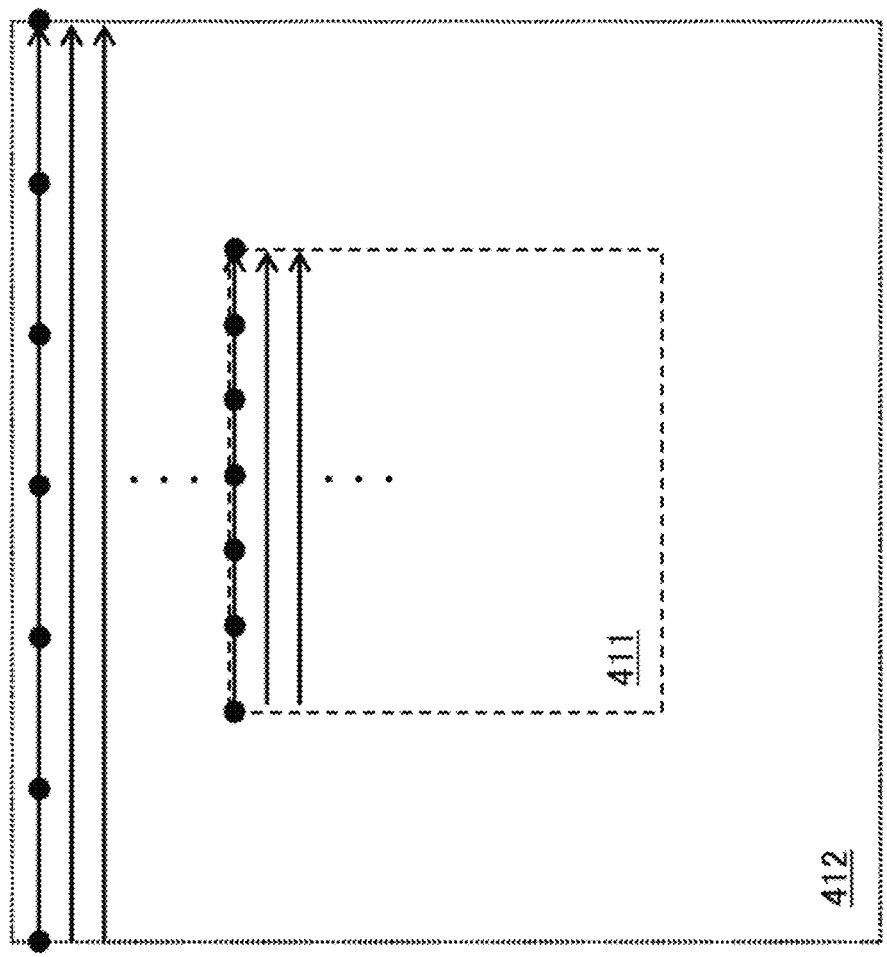

OPHTHALMIC IMAGING APPARATUS, CONTROLLING METHOD OF THE SAME, AND RECORDING MEDIUM

CROSS-REFERENCE TO RELATED APPLICATIONS

The present application is a continuation application of International Patent Application No. PCT/JP2019/031209, filed Aug. 7, 2019, claiming priority to Japanese Patent Application No. 2018-184102, filed Sep. 28, 2018, both of which are herein incorporated by reference in their entirety.

BACKGROUND OF THE INVENTION

Diagnostic imaging serves an important role in the field of ophthalmology. The utilization of optical coherence tomography (OCT) has advanced in recent years. OCT has come to be used not only for the acquisition of B-scan images and three dimensional images of eyes of subjects, but also for the acquisition of front images (en face images) such as C-scan images and shadowgrams.

In addition, techniques for constructing images that emphasize specific sites of subject's eyes have also been put into practical use. For example, OCT angiography, which is a technique of constructing images in which retinal blood vessels and/or choroidal blood vessels are emphasized, has been attracting attention (see Japanese Unexamined Patent Application Publication (Translation of PCT Application) No. 2015-515894, for example).

Generally, tissues (i.e., structures) in a scanned area do not change with time, but the blood flow inside blood vessels changes with time. OCT angiography emphasizes parts that exhibit such time-dependent changes (e.g., blood flow signals) and constructs an image.

OCT angiography is also referred to as OCT motion contrast imaging, and an image obtained by using OCT angiography is referred to as an angiographic image, an angiogram, a motion contrast image, or the like.

Typical conventional OCT angiography performs a three dimensional scan of a preset size (e.g., 9 mm×9 mm) and constructs an image representing a three dimensional distribution of eye fundus blood vessels. On the other hand, it is desired to acquire angiographic images of wider areas. Panoramic imaging is known as a technique for acquiring OCT data of a wide area of an eye fundus (see Japanese Unexamined Patent Application Publication No. 2009-183332, for example).

Panoramic imaging is an imaging technique of applying a three dimensional scan to each of a plurality of different regions, and composing a plurality of three dimensional images by the three dimensional scans to construct a wide area image. Typically, overlapping regions are set between regions adjacent to each other, and relative positions between adjacent images are determined on the basis of the overlapping regions. Further, the sequential application of the three dimensional scans to the plurality of different regions is typically implemented by control of an optical scanner and/or control of fixation positions.

A wide area image acquired by panoramic imaging is referred to as a panoramic image, a mosaic image, a montage image, or the like. In addition, panoramic imaging is also referred to as montage imaging or the like. Objects to be imaged (depicted, emphasized) by the motion contrast technique are not limited to blood flow, and may also depict any kind of object that changes with time. Further, the three dimensional scan applied to OCT angiography is typically a raster scan, but a Lissajous scan may also be employed in order to reduce adverse effects of fixation errors (see Japanese Unexamined Patent Application Publication No. 2018-068578, for example).

As described above, OCT angiography is carried out through repetitive photographing (scanning) of the same part (area, site) and generation of a motion contrast image on the basis of the temporal change obtained therefrom. Here, the range of detectable flow velocity depends on the rate of the repetitive photographing. If the repetition time interval is not constant, the detectable flow velocity range will also vary. Such variation in the detectable flow velocity range may cause inconvenience such that slow blood flows can be detected at some sites while cannot be detected at other sites. In other words, the variation may cause the sensitivity to flow velocity (flow velocity sensitivity) to be not constant, which in turn, may lead to a problem such as blood vessels that should be depicted are not depicted.

Further, while panoramic imaging may be used as a method of widening imaging areas of OCT angiography, it is supposed to employ contrivance for imaging efficiency, such as contrivance of preparing the various (uneven) sizes and/or the various (uneven) shapes of a plurality of regions to which a three dimensional scan is applied.

In addition, there are cases where a three dimensional scan mode other than a raster scan is used, such as the cases where a Lissajous scan is employed in order to reduce the adverse effects of fixation errors.

In all of the cases listed above, the repetitive imaging rate (the repetition time interval) needs to be constant over the entire imaging area in order to adjust the flow velocity sensitivity over the entire application area of OCT angiography and to enable calculation of relative flow velocity.

BRIEF SUMMARY OF THE INVENTION

According to the present disclosure, an ophthalmic imaging apparatus performs motion contrast imaging by applying optical coherence tomography (OCT) scanning to an eye, and comprises: a data acquiring unit configured to acquire a plurality of pieces of time-course data respectively corresponding to a plurality of scan points by repetitively applying an A-scan to each of the plurality of scan points, the A-scan being a one dimensional scan along a depth direction; an image constructing unit configured to construct a motion contrast image from the plurality of pieces of time-course data acquired by the data acquiring unit; and a controller configured to control the data acquiring unit such that data acquisition time intervals of first time-course data corresponding to a first scan point of the plurality of scan points and data acquisition time intervals of second time-course data corresponding to a second scan point become substantially equal to each other.

BRIEF DESCRIPTION OF SEVERAL VIEWS OF THE DRAWING

FIG. 5 is a schematic diagram for describing an example of processing performed by the ophthalmic imaging apparatus according to the embodiment example.

DETAILED DESCRIPTION OF THE INVENTION

Figure 1:
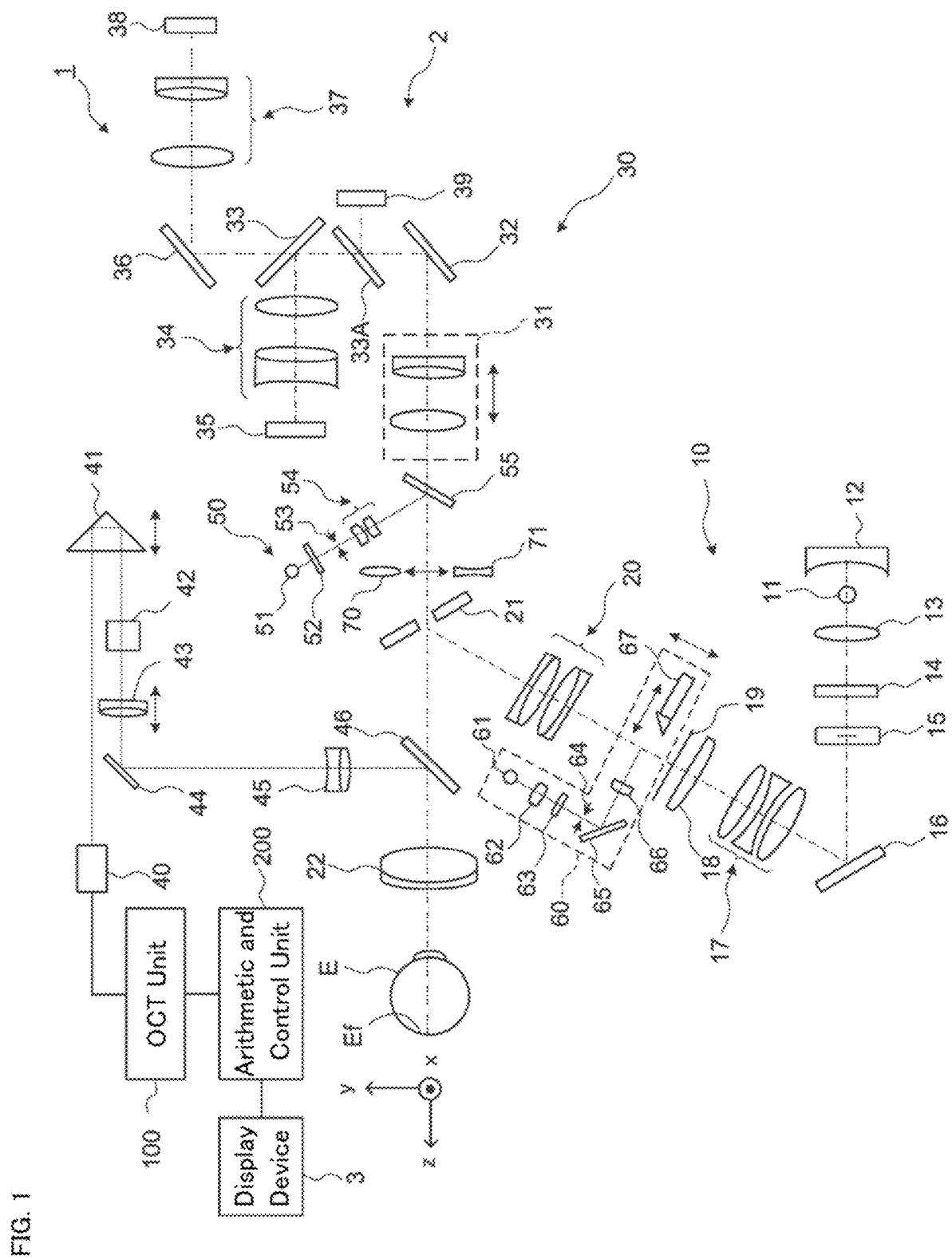
FIG. 1 is a schematic diagram illustrating an example of the configuration of the ophthalmic imaging apparatus according to the embodiment example.

An object of the present disclosure is to provide a technique for achieving a constant repetitive imaging rate in OCT angiography.

The first aspect example of some embodiments of the present disclosure is an ophthalmic imaging apparatus that performs motion contrast imaging by applying optical coherence tomography (OCT) scanning to an eye, comprising: a data acquiring unit configured to acquire a plurality of pieces of time-course data respectively corresponding to a plurality of scan points by repetitively applying an A-scan to each of the plurality of scan points, the A-scan being a one dimensional scan along a depth direction; an image constructing unit configured to construct a motion contrast image from the plurality of pieces of time-course data acquired by the data acquiring unit; and a controller configured to control the data acquiring unit such that data acquisition time intervals of first time-course data corresponding to a first scan point of the plurality of scan points and data acquisition time intervals of second time-course data corresponding to a second scan point become substantially equal to each other.

The second aspect example of some embodiments of the present disclosure is the ophthalmic imaging apparatus of the first aspect example, further comprising a first setting processor configured to set a first route and a second route, the first route being a moving route of an A-scan application position in a direction perpendicular to the depth direction between an A-scan application to the first scan point and a next A-scan application to the first scan point, and the second route being a moving route of an A-scan application position in a direction perpendicular to the depth direction between an A-scan application to the second scan point and a next A-scan application to the second scan point, wherein the controller controls the data acquiring unit based on the first route and the second route set by the first setting processor.

The third aspect example of some embodiments of the present disclosure is the ophthalmic imaging apparatus of the second aspect example, wherein the first setting processor sets the first route and the second route such that a first route length that is a length of the first route and a second route length that is a length of the second route are substantially equal to each other.

The fourth aspect example of some embodiments of the present disclosure is the ophthalmic imaging apparatus of the third aspect example, wherein the first setting processor sets scan point intervals of the first route and scan point intervals of the second route substantially equal to each other.

The fifth aspect example of some embodiments of the present disclosure is the ophthalmic imaging apparatus of any of the second to fourth aspect examples, wherein the first scan point is located on a first scan line and the second scan point is located on a second scan line, the first route is the first scan line and the second route is the second scan line, and the controller controls the data acquiring unit to repeat an OCT scan along the first scan line predetermined number of times consecutively and repeat an OCT scan along the second scan line predetermined number of times consecutively.

The sixth aspect example of some embodiments of the present disclosure is the ophthalmic imaging apparatus of any of the second to fifth aspect examples, wherein the data acquiring unit applies motion contrast imaging to both a first region and a second region that are different in at least one of a shape and a size, and the first scan point is located in the first region and the second scan point is located in the second region.

The seventh aspect example of some embodiments of the present disclosure is the ophthalmic imaging apparatus of the first aspect example, further comprising a second setting processor configured to set a first disposition and a second disposition, the first disposition being a disposition of scan points on a first route that is a moving route of an A-scan application position in a direction perpendicular to the depth direction between an A-scan application to the first scan point and a next A-scan application to the first scan point, and the second disposition being a disposition of scan points on a second route that is a moving route of an A-scan application position in a direction perpendicular to the depth direction between an A-scan application to the second scan point and a next A-scan application to the second scan point, wherein the controller controls the data acquiring unit based on the first disposition and the second disposition set by the second setting processor.

The eighth aspect example of some embodiments of the present disclosure is the ophthalmic imaging apparatus of the seventh aspect example, wherein the second setting processor sets scan point intervals of the first route and scan point intervals of the second route different from each other.

The ninth aspect example of some embodiments of the present disclosure is the ophthalmic imaging apparatus of the eighth aspect example, wherein the second setting processor sets a first route length that is a length of the first route and a second route length that is a length of the second route different from each other.

The tenth aspect example of some embodiments of the present disclosure is the ophthalmic imaging apparatus of any of the seventh to ninth aspect examples, wherein the second setting processor sets a number of the scan points on the first route and a number of the scan points on the second route substantially equal to each other.

The eleventh aspect example of some embodiments of the present disclosure is the ophthalmic imaging apparatus of any of the seventh to tenth aspect examples, wherein the first scan point is located on a first scan line and the second scan point is located on a second scan line, the first route is the first scan line and the second route is the second scan line, and the controller controls the data acquiring unit to repeat an OCT scan along the first scan line predetermined number of times consecutively and repeat an OCT scan along the second scan line predetermined number of times consecutively.

The twelfth aspect example of some embodiments of the present disclosure is the ophthalmic imaging apparatus of any of the seventh to eleventh aspect examples, wherein the data acquiring unit applies motion contrast imaging to both a first region and a second region that are different in at least one of a shape and a size, and the first scan point is located in the first region and the second scan point is located in the second region.

The thirteenth aspect example of some embodiments of the present disclosure is a method of controlling an ophthalmic imaging apparatus that performs motion contrast imaging by applying optical coherence tomography (OCT) scanning to an eye, comprising: a data acquiring step of acquiring a plurality of pieces of time-course data respectively corresponding to a plurality of scan points by repetitively applying an A-scan to each of the plurality of scan points, the A-scan being a one dimensional scan along a depth direction; a controlling step of executing, in parallel with the data acquiring step, control for causing data acquisition time intervals of first time-course data corresponding to a first scan point of the plurality of scan points and data acquisition time intervals of second time-course data corresponding to a second scan point to become substantially equal to each other; and an image constructing step of constructing a motion contrast image from the plurality of pieces of time-course data acquired by the data acquiring step.

The fourteenth aspect example of some embodiments of the present disclosure is a program causing a computer to execute the method of the thirteenth aspect example.

The fifteenth aspect example of some embodiments of the present disclosure is a computer-readable non-transitory recording medium that records the program of the fourteenth aspect example.

According to some embodiment examples of the present disclosure, the repetitive imaging rate in OCT angiography can be kept constant.

An ophthalmic imaging apparatus, a method of controlling the same, a program, and a recording medium according to some embodiment examples will be described in detail with referring to the drawings. The ophthalmic imaging apparatus of the embodiment example is an ophthalmic apparatus that has a function of performing optical coherence tomography (OCT), and is capable of performing OCT angiography. While OCT angiography of the embodiment example is applied to eye fundi, target sites of OCT angiography may be any site other than eye fundi such as anterior eye segments.

The following describes an ophthalmic imaging apparatus configured by combining a swept source OCT apparatus and a fundus camera; however, embodiment examples are not limited to such multifunction apparatuses. The type of OCT technique employed in embodiment examples is not limited to swept source OCT, and some embodiment examples may employ spectral domain OCT, for example.

Swept source OCT is an imaging technique to construct an image performed by: splitting light emitted from a wavelength tunable light source (also referred to as a wavelength swept light source) into measurement light and reference light; superposing return light of the measurement light returning from the object with the reference light to generate interference light; detecting the interference light by a detector such as a balanced photodiode; collecting data detected by the detector according to the wavelength sweeping and the measurement light scanning; and applying Fourier transform and other processing to the detection data collected.

Spectral domain OCT is an imaging technique to construct an image performed by: splitting light from a low coherence light source into measurement light and reference light; superposing return light of the measurement light returning from the object with the reference light to generate interference light; detecting the spectral distribution of the interference light with a spectrometer; and applying Fourier transform and other processing to the spectral distribution acquired by the spectrometer.

As described above, swept source OCT is an OCT technique for acquiring a spectral distribution by time division while spectral domain OCT is an OCT technique for acquiring a spectral distribution by space division. In addition, OCT techniques applicable to embodiment examples are not limited to these two. Some embodiment examples may employ any type of OCT techniques different from these, such as time domain OCT.

The ophthalmic imaging apparatus according to embodiment examples may or may not include a function of acquiring photographs (digital photographs) of subject's eyes. Typical examples of ophthalmic modalities having the digital photography function include a fundus camera, a scanning laser ophthalmoscope (SLO), a slit lamp microscope, an anterior eye segment imaging camera, and a surgical microscope. Front images such as fundus photographs may be used for eye fundus observation, scan area setting, tracking, and the like. Note that ophthalmic modalities usable for embodiment examples are not limited to these, and some embodiment examples may employ a modality other than ophthalmic modalities.

In the present specification, "image data" and an "image" based thereon are not distinguished from one another unless otherwise mentioned. Likewise, a "site" or "tissue" of the subject's eye and an "image" representing that site or that tissue are not distinguished from one another unless otherwise mentioned.

Now, the embodiment example provides examples of techniques for maintaining a repetitive imaging rate in OCT angiography constant. In general, the A-scan rate (repetition rate of A-scans) is constant in OCT angiography. Therefore, embodiment examples may employ any of the following methods in order to maintain the repetitive imaging rate constant: (1) maintaining constant the length of the route (path) of the scanning performed between an application of an A-scan to an arbitrary location and an application of the next A-scan to the same location; and (2) adjusting the disposition (arrangement, layout, array) of A-scans.

The ophthalmic imaging apparatus 1 shown in FIG. 1 of the embodiment example includes the fundus camera unit 2, the OCT unit 100, and the arithmetic and control unit 200. The fundus camera unit 2 is provided with optical systems and mechanisms for acquiring front images of the subject's eye E, and optical systems and mechanisms for performing OCT. The OCT unit 100 includes optical systems and mechanisms for performing OCT. The arithmetic and control unit 200 includes one or more processors configured to execute various processes (e.g., calculations, operations, and controls). In addition to them, the ophthalmic imaging apparatus 1 may also include arbitrary kinds of elements such as a member for supporting the face of the subject (e.g., a chin rest and/or a forehead rest), and/or arbitrary kinds of units such as a lens unit for switching the sites to which OCT is applied. An example of such a lens unit is an attachment for anterior eye segment OCT.

In the present specification, the term "processor" is used to mean, for example, a circuit (circuitry) such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. For example, a processor of some embodiment examples loads and executes a program stored in a storage circuit (circuitry) or a storage device, thereby implementing functions according to the embodiment example.

The fundus camera unit 2 is provided with optical systems for photographing the fundus Ef of the subject's eye E. Digital images of the fundus Ef (referred to as fundus images, fundus photographs, or the like) obtained by the fundus camera unit 2 are, in general, front images such as observation images and photographed images. An observation image is obtained by capturing a moving image using near-infrared light. A photographed image is a still image obtained by using flash light in the visible range.

The fundus camera unit 2 includes the illumination optical system 10 and the photographing optical system 30. The illumination optical system 10 projects illumination light onto the subject's eye E. The photographing optical system 30 detects the return light of the illumination light projected onto the subject's eye E. The measurement light incident from the OCT unit 100 is directed to the subject's eye E through the optical path in the fundus camera unit 2. The return light of the measurement light projected onto the subject's eye E (e.g., the fundus Ef) is directed to the OCT unit 100 through the same optical path in the fundus camera unit 2.

The light output from the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, passes through the relay lens system 17, the relay lens 18, the diaphragm 19, and the relay lens system 20, and is directed to the aperture mirror 21. Then, the observation illumination light is reflected on the peripheral part (i.e., the surrounding area of the aperture part) of the aperture mirror 21, penetrates the dichroic mirror 46, and is refracted by the objective lens 22, thereby illuminating the subject's eye E (the fundus Ef thereof). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the return light passes through the half mirror 33A, is reflected by the dichroic mirror 33, and forms an image on the light receiving surface of the image sensor 35 by the imaging lens 34. The image sensor 35 detects the return light at a predetermined frame rate (capture rate). Note that the focus of the photographing optical system 30 is adjusted to position on the fundus Ef or the anterior eye segment.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (i.e., a fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef. Fixation targets are typically used for guidance and fixation of the line of sight. The direction in which the line of sight of the subject's eye E is guided (and fixed), that is, the direction in which the fixation of the subject's eye E is urged is referred to as a fixation position.

By changing the display position of the fixation target image on the screen of the LCD 39, the fixation position of the subject's eye E by the fixation target can be changed. Examples of the fixation position includes the following: a fixation position for acquiring an image centered on the macula; a fixation position for acquiring an image centered on the optic nerve head; a fixation position for acquiring an image centered on a position that is located between the macula and the optic nerve head (fundus center position); and a fixation position for acquiring an image of a site far away from the macula (i.e., peripheral part of the fundus).

A user interface such as a graphical user interface (GUI) for designating at least one of such typical fixation positions can be provided. Further, a user interface such as a GUI for manually changing the fixation position (i.e., the display position of the fixation target) can be provided. In addition, it is also possible to employ a configuration of setting the fixation position automatically.

The configuration for presenting the fixation target, which is used for changing the fixation position, to the subject's eye E is not limited to display devices such as LCDs. For example, a device can be adopted, in place of a display device, which includes a plurality of light emitting elements (e.g., light emitting diodes) that are disposed in a matrix-like arrangement. Such a device is referred to as a fixation matrix. If this is the case, the fixation position of the subject's eye E made by the fixation target can be changed by turning on the plurality of light emitting elements in a selective manner. As another example, a device provided with one or more movable light emitting elements may be employed for generating a fixation target usable for changing the fixation position.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The return light of the alignment light from the subject's eye E (the cornea reflection light, etc.) passes through the same route as that of the return light of the observation illumination light and is guided to the image sensor 35. Based on the received image (referred to as the alignment indicator image), manual alignment and/or automatic alignment may be performed.

The focus optical system 60 generates a split indicator used for the focus adjustment with respect to the subject's eye E. In conjunction with the movement of the photography focusing lens 31 along the optical path of the photographing optical system 30 (referred to as the photographing optical path), the focus optical system 60 is moved along the optical path of the illumination optical system 10 (referred to as the illumination optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, and passes through the two-hole diaphragm 64. Then, the focus light is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The return light of the focus light from the subject's eye E (e.g., the fundus reflection light) passes through the same route as the return light of the alignment light and is guided to the image sensor 35. Based on the image (referred to as the split indicator image), manual focusing and/or automatic focusing can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT (measurement arm). The dichroic mirror 46 reflects the light of wavelength bands used for OCT and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions of the arrows shown in FIG. 1. Thereby, the length of the measurement arm is changed. The change in the measurement arm length can be utilized for correcting the optical path length according to the axial length and for adjusting the interference condition, for example.

Together with the dispersion compensation member 113 (described later) arranged in the reference arm, the dispersion compensation member 42 acts to equalize the dispersion characteristics of the measurement light LS and the dispersion characteristics of the reference light LR with each other.

The OCT focusing lens 43 is movable along the measurement arm in order to perform the focus adjustment of the measurement arm. Also, the ophthalmic imaging apparatus 1 may be configured to control the movement of the photography focusing lens 31, the movement of the focus optical system 60, and the movement of the OCT focusing lens 43 in an interlocking manner.

The optical scanner 44 is placed at a position substantially optically conjugate with the pupil of the subject's eye E. The optical scanner 44 deflects the measurement light LS guided through the measurement arm. An example of the optical scanner 44 is a galvano scanner that allows two dimensional scanning (two dimensional deflection of light). Typically, the optical scanner 44 includes a one dimensional scanner for deflecting the measurement light in the +x and −x directions, and another one dimensional scanner for deflecting the measurement light in the +y and −y directions. If this is the case, for example, either one of the one dimensional scanners may be placed at a position optically conjugate with the pupil, or a position optically conjugate with the pupil is positioned at a position between the one dimensional scanners.

Figure 2:
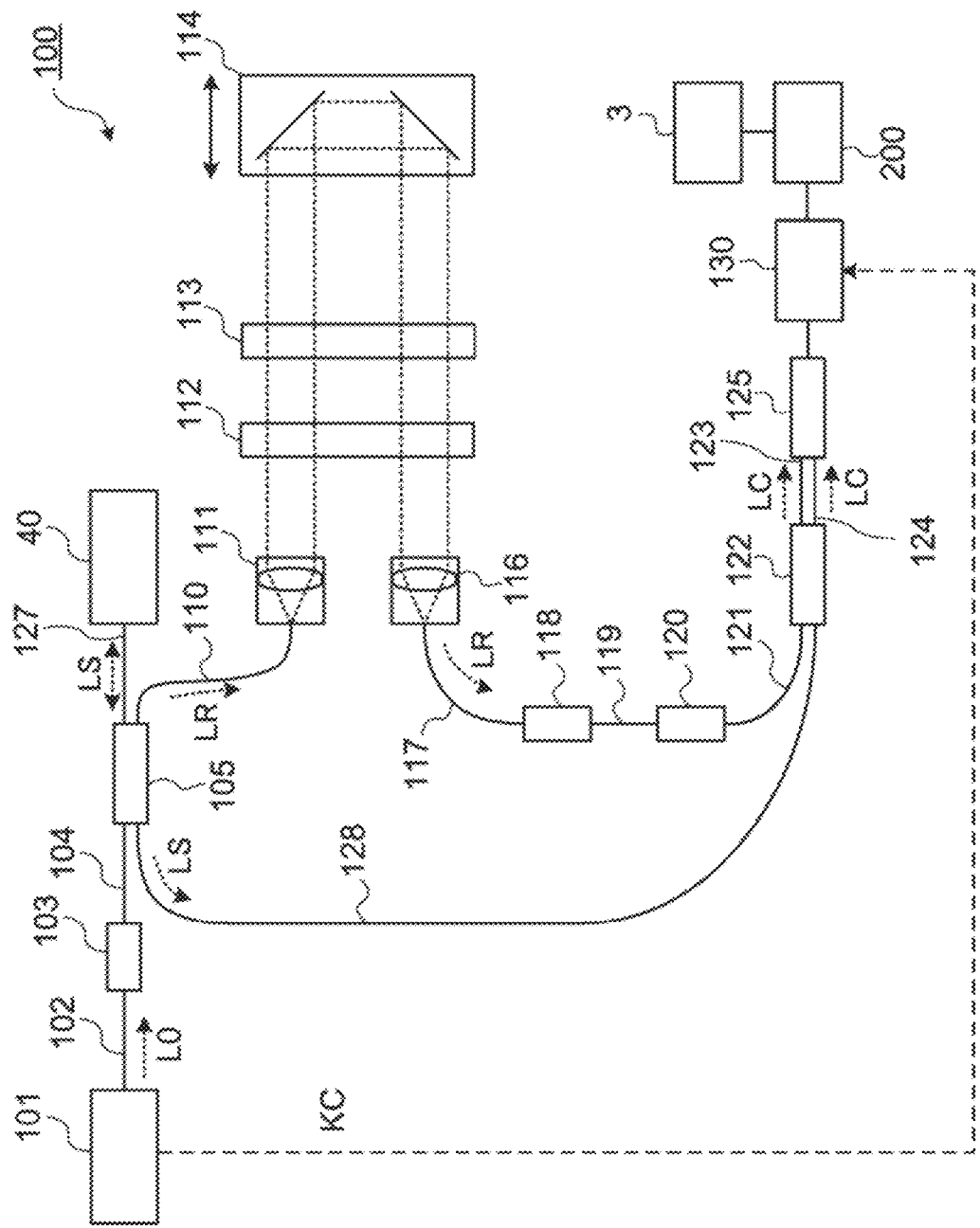
FIG. 2 is a schematic diagram illustrating an example of the configuration of the ophthalmic imaging apparatus according to the embodiment example.

The OCT unit 100 shown in FIG. 2 of the embodiment example is provided with the optical system for performing swept source OCT. The optical system includes an interference optical system. The interference optical system is configured to split light emitted from a wavelength tunable light source into measurement light and reference light, superpose the return light of the measurement light projected onto the subject's eye E with the reference light having traveled through the reference optical path to generate interference light, and detect the interference light. The data (detection signal) obtained by the detection of the inference light is a signal representing a spectrum of the interference light. The detection signal is sent to the arithmetic and control unit 200.

The light source unit 101 includes, for example, a near infrared tunable laser configured to vary the wavelengths of emitted light at high speed. The light LO output from the light source unit 101 is guided to the polarization controller 103 through the optical fiber 102, and the polarization state of the light LO is regulated. Further, the light LO is guided to the fiber coupler 105 through the optical fiber 104 and is split into the measurement light LS and the reference light LR. The optical path of the measurement light LS is referred to as a measurement arm, a sample arm, or the like, and the optical path of the reference light LR is referred to as a reference arm or the like.

The reference light LR generated by the fiber coupler 105 is guided through the optical fiber 110 to the collimator 111, is converted into a parallel light beam, travels through the optical path length correction member 112 and the dispersion compensation member 113, and is guided to the retroreflector 114. The optical path length correction member 112 acts to coincide the optical path length of the reference light LR and the optical path length of the measurement light LS with each other. Together with the dispersion compensation member 42 arranged in the measurement arm, the dispersion compensation member 113 acts to equalize the dispersion characteristics of the reference light LR and the dispersion characteristics of the measurement light LS with each other. The retroreflector 114 is movable along the optical path of the reference light LR incident on the retroreflector 114. With this, the length of the reference arm is changed. The change in the reference arm length can be utilized, for example, for the correction of the optical path length according to the axial length, and for the regulation of the interference condition.

After passing through the retroreflector 114, the reference light LR travels through the dispersion compensation member 113 and the optical path length correction member 112, is converted from a parallel light beam to a convergent light beam by the collimator 116, and is incident on the optical fiber 117. The reference light LR having entered the optical fiber 117 is guided to the polarization controller 118, and the polarization state of the reference light LR is regulated. The reference light LR having guided to the polarization controller 118 is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided to the collimator lens unit 40 through the optical fiber 127 and is converted to a parallel light beam. The measurement light LS, then, passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. The return light of the measurement light LS returned from the subject's eye E travels along the measurement arm in the opposite direction, is directed to the fiber coupler 105, and then reaches the fiber coupler 122 via the optical fiber 128.

The fiber coupler 122 superposes the measurement light LS incident through the optical fiber 128 with the reference light LR incident through the optical fiber 121, to generate interference light. The fiber coupler 122 splits the generated interference light at a predetermined splitting ratio (e.g., the ratio is 1 to 1) to generate a pair of the interference light LC. The pair of the interference light LC is guided to the detector 125 respectively through the optical fibers 123 and 124.

The detector 125 includes, for example, a balanced photo diode. The balanced photodiode includes a pair of photodetectors for respectively detecting the pair of the interference light LC, and outputs the difference between a pair of detection signals obtained by the pair of photodetectors. The detector 125 sends the output (i.e., detection signal such as the difference signal) to the data acquisition system (DAQ) 130.

The clock KC is supplied from the light source unit 101 to the data acquisition system 130. The clock KC is generated in the light source unit 101 in synchronization with the output times of the respective wavelengths varied within a predetermined wavelength range by the wavelength tunable type light source. For example, the light source unit 101 splits the light LO of each output wavelength to generate two pieces of split light, applies an optical delay to one of the two pieces of split light, superposes the two pieces of split light with each other, detects the superposed light, and generates the clock KC based on the detection signal of the superposed light. The data acquisition system 130 uses the clock KC to perform the sampling of the detection signal (difference signal) input from the detector 125. The data acquisition system 130 sends the data extracted by the sampling of the detection signal to the arithmetic and control unit 200.

The present example configuration is provided with both an element for changing the measurement arm length (e.g., the retroreflector 41) and an element for changing the reference arm length (e.g., the retroreflector 114 or a reference mirror); however, only one of these two elements may be provided in some other embodiment examples. Elements for changing the difference between the measurement arm length and the reference arm length (i.e., elements for changing the optical path length difference) are not limited to the aforesaid elements, and some aspect examples may employ any type of element such as any type of optical members or any type of mechanisms.

The arithmetic and control unit 200 controls each part of the fundus camera unit 2, the display device 3, and the OCT unit 100. Further, the arithmetic and control unit 200 executes various kinds of arithmetic processes. For example, the arithmetic and control unit 200 applies signal processing such as Fourier transform on a spectral distribution generated based on a sampling data group acquired by the data acquisition system 130 for each series of wavelength scanning (wavelength sweeping), that is, for individual A-lines. Thereby, the arithmetic and control unit 200 creates reflection intensity profiles for the A-lines respectively. Furthermore, the arithmetic and control unit 200 applies imaging processing to the reflection intensity profiles for the A-lines to construct image data. Arithmetic processes for the image data construction may be the same as those of conventional swept source OCT.

The arithmetic and control unit 200 includes, for example, one or more processors, random access memory (RAM), read only memory (ROM), hard disk drive, and communication interface. A storage device such as the hard disk drive stores various kinds of computer programs. The arithmetic and control unit 200 may include an operation device, an input device, a display device, and the like.

Figure 3:
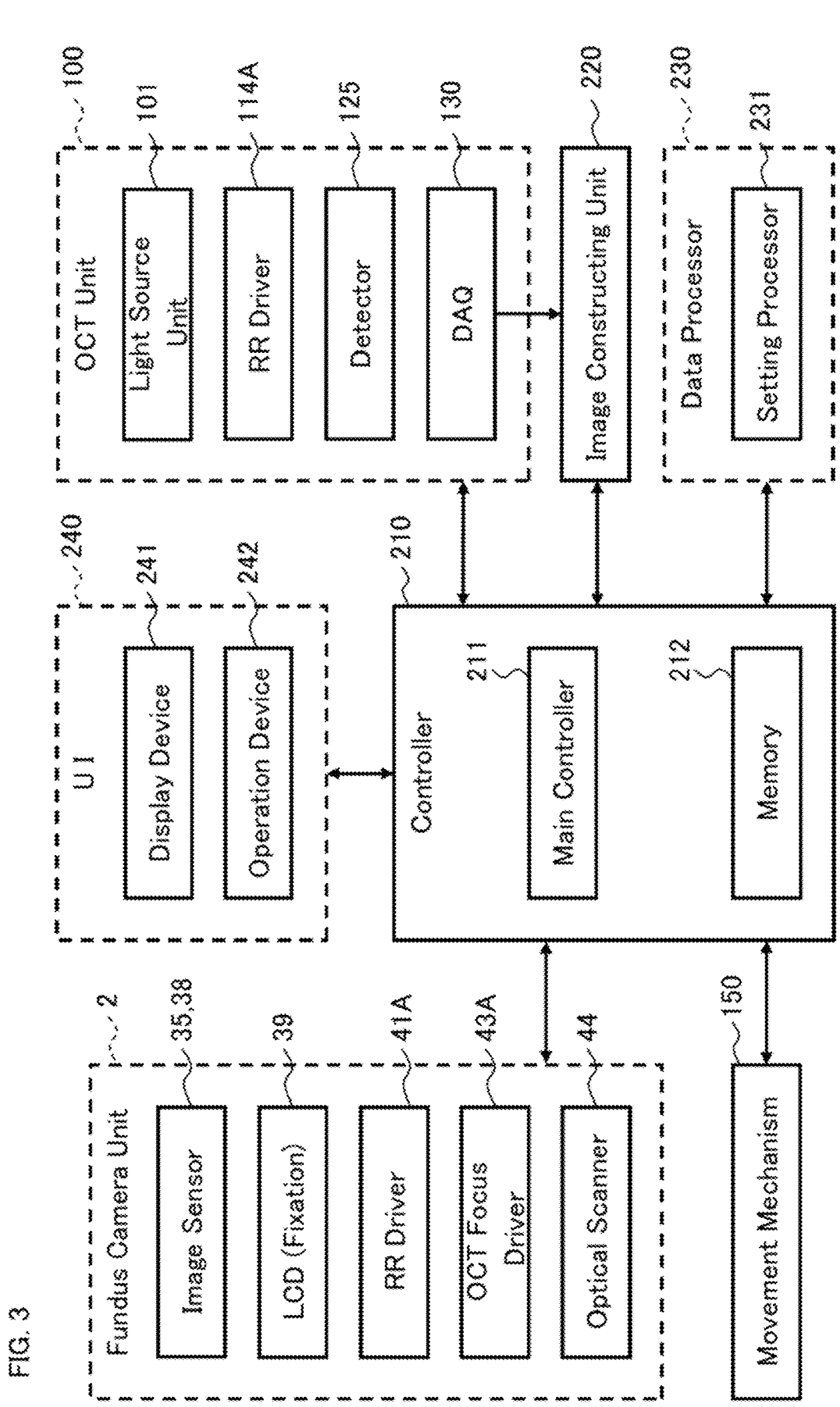
FIG. 3 is a schematic diagram illustrating an example of the configuration of the ophthalmic imaging apparatus according to the embodiment example.

FIG. 3 shows an example of the configuration of the control system (processing system) of the ophthalmic imaging apparatus 1. The controller 210, the image constructing unit 220, and the data processor 230 may be provided in the arithmetic and control unit 200, for example.

The controller 210 includes one or more processors and controls each part of the ophthalmic imaging apparatus 1. The controller 210 includes the main controller 211 and the memory 212.

The main controller 211 includes one or more processors and controls each element of the ophthalmic imaging apparatus 1 (including the elements shown in FIG. 1 to FIG. 3). The main controller 211 is implemented by the cooperation of hardware including a circuit (circuitry) and control software.

The photography focusing lens 31 disposed in the photographing optical path and the focus optical system 60 disposed in the illumination optical path are moved by a photography focus driver (not shown in the drawings) under the control of the main controller 211. The retroreflector 41 disposed in the measurement arm is moved by the retroreflector driver (RR driver, for short) 41A under the control of the main controller 211. The OCT focusing lens 43 disposed in the measurement arm is moved by the OCT focus driver 43A under the control of the main controller 211. The optical scanner 44 disposed in the measurement arm operates under the control of the main controller 211. The retroreflector 114 disposed in the reference arm is moved by the retroreflector driver (RR driver, for short) 114A under the control of the main controller 211. Each of the aforesaid drivers includes an actuator, such as a pulse motor, that operates under the control of the main controller 211.

The movement mechanism 150 moves, for example, at least the fundus camera unit 2 in a three dimensional manner. In a typical example, the movement mechanism 150 includes the following: an x-stage movable in the +x and −x directions (i.e., left and right directions); an x-movement mechanism that moves the x-stage; a y-stage movable in the +y and −y directions (i.e., up and down directions); a y-movement mechanism that moves the y-stage; a z-stage movable in the +z and −z directions (i.e., depth direction); and a z-movement mechanism that moves the z-stage. Each of the movement mechanisms described here includes an actuator, such as a pulse motor, that operates under control of the main controller 211.

The main controller 211 can execute OCT scanning, such as OCT angiography and panoramic OCT angiography, based on the conditions set by the setting processor 231 described later.

The memory 212 stores various kinds of data. Examples of the data stored in the memory 212 include image data of OCT images, image data of fundus images, and subject's eye information. The subject's eye information includes subject information such as patient IDs and patient's names, identification information for the left eye and the right eye, and electronic medical record information.

The image constructing unit 220 constructs image data based on data acquired by the data acquisition system 130. The image constructing unit 220 includes one or more processors. The image constructing unit 220 is implemented by the cooperation of hardware including a circuit (circuitry) and image constructing software.

The image constructing unit 220 constructs cross sectional image data based on the data acquired by the data acquisition system 130. The cross sectional image data construction processing includes signal processing such as noise elimination (or noise reduction), filtering, fast Fourier transform (FFT), and other processes as in conventional swept source OCT.

The image data constructed by the image constructing unit 220 is a data set including a group of a plurality of pieces of image data, that is, a group of a plurality of pieces of A-scan image data or an A-scan image data group. The A-scan image data group is constructed by applying imaging processing to the reflection intensity profiles respectively at the A-lines. The A-lines are arranged in the area to which OCT scanning has been applied. Each of the A-lines is a scan line lying along the z direction.

The image data constructed by the image constructing unit 220 may be one or more pieces of B-scan image data or stack data. The stack data is constructed by embedding a plurality of pieces of B-scan image data in a single three dimensional coordinate system. The image constructing unit 220 may apply processes including interpolation processing to stack data, thereby constructing volume data (voxel data). Stack data and volume data are typical examples of three dimensional image data. Three dimensional image data is image data that is represented by a three dimensional coordinate system.

When OCT angiography is conducted, the main controller 211 performs repetitive scanning on the same region of the fundus Ef a predetermined number of times. The image constructing unit 220 can construct a motion contrast image based on a data set collected through the repetitive scanning conducted by the data acquisition system 130. The motion contrast image thus constructed is an angiographic image created by emphasizing time course variations in interference signals caused by blood flows in the fundus Ef. Some typical aspect examples are configured to apply OCT angiography to a three dimensional region of the fundus Ef, and to construct an image representing a three dimensional distribution of blood vessels of the fundus Ef.

The image constructing unit 220 may be configured to apply image processing to the three dimensional image data constructed. For example, the image constructing unit 220 may construct new image data by applying rendering to the three dimensional image data. Examples of techniques of the rendering include volume rendering, maximum intensity projection (MIP), minimum intensity projection (MinIP), surface rendering, and multi planar reconstruction (MPR). Further, the image constructing unit 220 may be configured to construct projection data by applying, to the three dimensional image data, image projection in the z direction (i.e., the A-line direction or the depth direction). In addition, the image constructing unit 220 may be configured to construct a shadowgram by applying, to only a part of the three dimensional image data, image projection in the z direction. Note that the part of the three dimensional image data to be subject to the image projection for the shadowgram construction is determined by using segmentation described later, for example.

After conducting OCT angiography, the image constructing unit 220 can construct any kind of two dimensional angiographic image data and/or any kind of pseudo three dimensional angiographic image data, from three dimensional angiographic image data. For example, the image constructing unit 220 may construct two dimensional angiographic image data representing an arbitrary cross section of the fundus Ef by applying multi planar reconstruction to three dimensional angiographic image data. In addition, the image constructing unit 220 may construct a front image from a slab determined by applying segmentation to three dimensional angiographic image data.

The data processor 230 performs various kinds of data processing. For example, the data processor 230 may be configured to apply image processing and/or analysis processing to OCT image data, and/or, apply image processing and/or analysis processing to observation image data and/or photographed image data. The data processor 230 includes, for example, at least one of one or more processors and one or more dedicated circuit boards.

The data processor 230 includes the setting processor 231. The setting processor 231 is configured to set one or more scan conditions for OCT angiography. The description below starts with an account of an example of OCT angiography carried out using the ophthalmic imaging apparatus 1.

In OCT angiography, setting of a plurality of scan points to each of which A-scans are to be applied is performed. Typical OCT angiography employs a raster scan consisting of a plurality of B-scans parallel to each other, and each of the B-scans consists of a plurality of A-scans. The scan points are the positions (locations) to each of which A-scans are to be applied.

The ophthalmic imaging apparatus 1 acquires time-course data corresponding to each scan point by repetitively applying an A-scan to each scan point. In some typical aspect examples, the number of the repetitions of an A-scan for each scan point is determined in advance, and the number of repetitions is set to four, for example.

As an example of OCT motion contrast imaging in the case where a raster scan is employed, the ophthalmic imaging apparatus 1 may perform the following processes: a process of applying an OCT scan (B-scan) to a scan line a predetermined number of times in succession; and then a process of applying a B-scan for the next scan line the predetermined number of times in succession. Also, the present example applies such repetitive OCT scanning to the plurality of scan lines constituting the raster scan in a sequential manner according to a predetermined order. In other words, the ophthalmic imaging apparatus 1 may perform the repetitive scanning in units of each of the plurality of scan lines constituting the raster scan.

As another example of OCT motion contrast imaging in the case where a raster scan is employed, the ophthalmic imaging apparatus 1 may perform repetitive scanning in units of a scan line group that consists of two or more scan lines. More specifically, the ophthalmic imaging apparatus 1 may sequentially apply one OCT scan (B-scan) to each of two or more scan lines included in one scan line group, and executes such sequential scanning a predetermined number of times. Subsequently, the ophthalmic imaging apparatus 1 applies the same OCT scanning to the next scan line group. The present example applies such repetitive OCT scanning to a plurality of scan line groups included in the raster scan in a sequential manner in accordance with a predetermined order. As a result of this, the repetitive OCT scanning can be carried out for every scan line of the raster scan.

The OCT motion contrast imaging as illustrated above allows the ophthalmic imaging apparatus 1 to acquire time-course data corresponding to every scan point. The time-course data includes a number of pieces of data corresponding to the number of A-scan repetitions. A typical example of the time-course data includes a number of pieces of data equal to the number of A-scan repetitions. Note that OCT motion contrast imaging may be conducted in the same or similar manner also in the case where a scan mode other than a raster scan is employed.

The setting processor 231 is configured to set one or more scan conditions for OCT motion contrast imaging. More specifically, the setting processor 231 may set one or more scan conditions such that an OCT scan is to be repetitively applied at constant time intervals (equal time intervals or same time intervals) for a plurality of scan points to which OCT motion contrast imaging is to be applied.

Stated differently, the setting processor 231 sets one or more scan conditions such that the time intervals of the repetitive OCT scanning (repetitive imaging rate) for any first scan point among the plurality of scan points to which OCT motion contrast imaging is applied and the repetitive imaging rate for any second scan point become substantially equal to each other.

As a result of such scan condition setting, the data acquisition time intervals of the first time-course data corresponding to the first scan point and the data acquisition time intervals of the second time-course data corresponding to the second scan point become substantially equal to each other. The data acquisition time intervals are the differences (intervals) in the acquisition times (acquisition time points) of a plurality of pieces of data included in time-course data, and are parameters equivalent to the repetitive imaging rate.

Note that the difference in repetitive imaging rates between different scan points (that is, the difference in data acquisition time intervals corresponding to different scan points) does not have to be zero, and an error may be allowed if the error belongs to a range for which a predetermined purpose can be achieved. The predetermined purpose may be any of the following, for example: for obtaining the same or equivalent flow velocity sensitivity for different scan points; and for being capable of comparing the flow velocities obtained for different scan points (that is, for being capable of calculating the relative flow velocities between different scan points).

As mentioned above, any of the following methods may be employed in the present embodiment example in order to set one or more scan conditions that makes the repetitive imaging rate constant between multiple scan points: (1) a method of maintaining constant the length of the route of a scan performed between an A-scan application to a scan point and the next A-scan application to the same scan point; (2) a method of adjusting the disposition (arrangement, layout, array) of A-scans. It should be noted that the A-scan speed (the repetition rate of the A-scan) is assumed to be constant as mentioned above. In other words, the time interval between a A-scan and the next A-scan is assumed to be constant.

The setting processor 231 may be configured to be capable of setting either one or both of: one or more scan conditions corresponding to the above method (1); and one or more scan conditions corresponding to the above method (2).

A description will be given of the case in which the method (1) is employed. As an example, suppose that a raster scan includes M scan lines SL(m) (m=1, 2, ..., M), and each scan line SL(m) includes N scan points SP(m, n) (n=1, 2, ..., N). Here, the index "m" indicates the order in which B-scans are applied to the scan lines SL(1) to SL(M), and the index "n" indicates the order in which A-scans are applied to the scan points SP(m, 1) to SP(m, N).

Here, the M scan lines SL(m) each include the same number of scan points (N scan points). Further, the M scan lines SL(m) may or may not have the same length.

Suppose that the scan point SP(m1, n1) is the first scan point, and that the scan point SP(m2, n2) different from the first scan point is the second scan point. Accordingly, at least one of "m1≠m2" and "n1≠n2" is satisfied.

In addition, suppose that the repetitive scanning is executed in units of each of the scan lines SL(m). That is, after applying the repetitive scan to the scan line SL(m), the repetitive scan is applied to the scan line SL(m+1) (here, m=1, 2, ..., M−1). Note that although a description is omitted for the above-mentioned case in which repetitive scanning is performed in units of a scan line group consisting of two or more scan lines, the same or similar processing as or to the following can be applied to such a case.

During the period of time between an A-scan application to the first scan point SP(m1, n1) and the next A-scan application to the same first scan point SP(m1, n1), scanning is performed for other N−1 scan points SP(m1, n) (n=1, 2, ..., N; n n1) that belong to the scan line SL(m1). In this case, the route (the first route) of the scanning performed during this period of time is the scan line SL(m1), and the length of the first route is equal to the length of the scan line SL(m1).

Likewise, during the period of time between an A-scan application to the second scan point SP(m2, n2) and the next A-scan application to the same second scan point SP (m2, n2), scanning is performed for other N−1 scan points SP(m2, n) (n=1, 2, ..., N; n n2) that belong to the scan line SL(m2). In this case, the route (the second route) of the scanning performed during this period of time is the scan line SL(m2), and the length of the second route is equal to the length of the scan line SL(m2).

In the case where the method (1) is employed, the setting processor 231 may be configured to set the first route (the scan line SL(m1)) and the second route (the scan line SL(m2)) such that the above conditions are satisfied. Note that a scan line(s) may be set such that only a part of the scan points belonging to the raster scan meets the above conditions. However, typical embodiment examples may set all the scan lines such that all the scan points satisfy the above conditions.

In the present example, the setting processor 231 may set the scan line SL(m1) and the scan line SL(m2) such that the first route length that is the length of the scan line SL (m1) and the second route length that is the length of the scan line SL(m2) are substantially equal to each other. Typical embodiment examples may set M scan lines SL(m) of substantially equal length.

In addition to this, the setting processor 231 may set the scan point intervals of the scan line SL(m1) and the scan point intervals of the scan line SL(m2) substantially equal to each other. In other words, the setting processor 231 may set the scan line SL(m1) and the scan line SL(m2) such that the scan lines SL(m1) and SL(m2) include the same number of scan points arranged with the same scan point intervals. Typical embodiment examples may set M scan lines SL(m) in which the same number of scan points are disposed at the same intervals.

The ophthalmic imaging apparatus 1 is capable of performing panoramic OCT angiography. More specifically, the ophthalmic imaging apparatus 1 is capable of constructing a wide area motion contrast image by applying OCT motion contrast imaging to each of a plurality of regions different from each other. The wide area motion contrast image is a mosaic image created by combining (synthesizing, composing) a plurality of motion contrast images corresponding to the plurality of regions respectively.

As mentioned earlier, it is conceivable to prepare a plurality of regions having a variety of the morphology in order to improve the efficiency of panoramic OCT angiography. Here, examples of the region morphology include shape and size. In the case of applying OCT motion contrast imaging to the first region and the second region that are mutually different in at least one of shape and size, a scan point belonging to the first region may be chosen to be the first scan point, and a scan point belonging to the second region may be chosen to be the second scan point. As a result of this, the lengths of scan lines respectively belonging to different regions can be made substantially equal.

Figure 4:
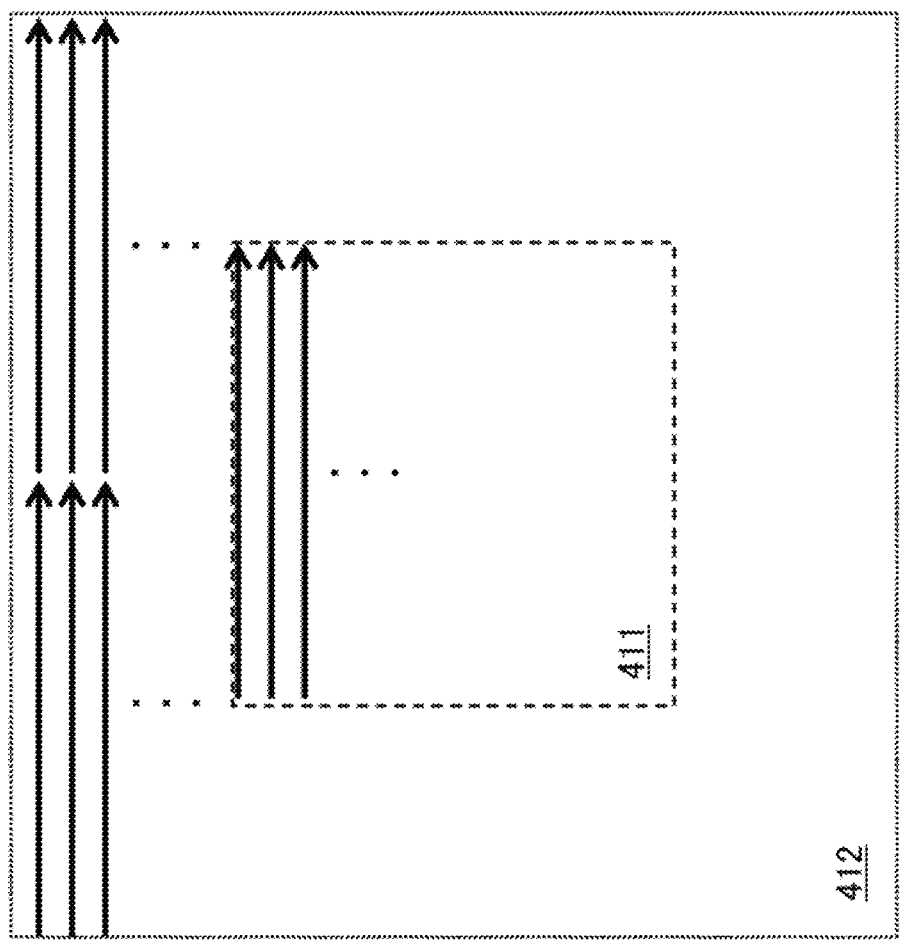
FIG. 4 is a schematic diagram for describing an example of processing performed by the ophthalmic imaging apparatus according to the embodiment example.

FIG. 4 shows a specific example. In the present example, the entire region, which is a square-shaped area in the xy plane, is divided into the central part region 411 and the peripheral part region 412. Typically, the central part region 411 is located in the central area of the fundus Ef and the peripheral region 412 is located in the peripheral area of the fundus Ef. The central part region 411 is a square-shaped area in the xy plane. The peripheral part region 412 has a shape defined by two concentric squares in the xy plane. The outer edge of the central part region 411 and the inner edge of the peripheral part region 412 are common.

Each arrow shown in FIG. 4 indicates a scan line. The width of the central part region 411 (the lengths of its sides) is half the outer size of the peripheral part region 412 (the lengths of the sides constituting its outer edge). A scan mode for the central part region 411 is a raster scan that consists of a plurality of scan lines (B-scans) having the lengths equal to the width of the central part region 411.

As for the peripheral part region 412, at least the region above the central part region 411 in FIG. 4 is scanned by a plurality of B-scans having the lengths equal to the width of the central part region 411. Note that as shown in FIG. 4, the end point of a B-scan coincides with the start point of another B-scan. In other words, by arranging two raster scans, each of which consisting of a plurality of B-scans having the same length as the width of the central part region 411, in the direction along the B-scans, that is, by arranging the two raster scans in the direction perpendicular to the B-scan disposition direction in the raster scans, (a part of) the peripheral part region 412 having the outer size that is twice the width of the central part region 411 is scanned.

Such equalization of B-scan lengths (scan line lengths) allows the repetitive imaging rate between the scan points to be constant (equal, same, uniform), allows equivalent sensitivities in flow velocity to be obtained for different scan points, and allows relative flow velocities to be calculated. This concludes the description of the example where the above method (1) is employed.

Further, by placing the central part region 411 in the central area of the fundus Ef and by placing the peripheral part region 412 in the peripheral area of the fundus Ef, the ophthalmic imaging apparatus 1 becomes capable of conducting scanning of the central part region 411 under (substantially) a constant (same, equivalent) focus condition (e.g., focal position, focal length) and (substantially) a constant OCT optical path length condition, as well as conducting scanning of the peripheral part region 412 under (substantially) a constant focus condition and (substantially) a constant OCT optical path length condition. Determining a plurality of regions on the basis of (in consideration of, according to) the eye fundus shape as in the present example allows the efficiency of panoramic OCT angiography to be improved.

Next, a description will be given of the case in which the method (2) is employed. The present example is configured to perform adjustment of A-scan arrangement in order to maintain the repetitive imaging rate between the scan points constant. Below, as in the description of the method (1), suppose that a raster scan includes M scan lines SL(m) (m=1, 2, . . . , M), and each scan line SL(m) includes N scan points SP(m, n) (n=1, 2, . . . , N). Further, the scan point SP(m1, n1) is the first scan point, and the scan point SP(m2, n2) different from the first scan point is the second scan point.

The setting processor 231 may be configured to set the first disposition (first arrangement, first layout, first array) and the second disposition (second arrangement, second layout, second array). Here, the first disposition is a disposition of scan points SP(m1, n) on the first route (the scan line SL(m1)) mentioned above, and the second disposition is a disposition of scan points SP(m2, n) on the second route (the scan line SL(m2)) mentioned above. Note that a scan line(s) may be set such that only a part of the scan points belonging to the raster scan meets the above conditions. However, typical embodiment examples may set the scan point disposition such that all the scan points satisfy the above conditions.

The setting processor 231 of the present example may choose mutually different values for the scan point intervals of the scan line SL(m1) and the scan point intervals of the scan line SL(m2).

For example, the setting processor 231 may set the length of the scan line SL(m1) and the length of the scan line SL(m2) different from each other.

In the case where the length of the scan line SL(m1) and the length of the scan line SL(m2) are different from each other, the number of the scan points belonging to the scan line SL(m1) and the number of the scan points belonging to the scan line SL(m2) may be made equal. In other words, the setting processor 231 may set the scan line SL(m1) and the scan line SL(m2) such that they have the same number of scan points but the scan points are disposed at different intervals from each other. Some typical aspect examples may set M scan lines SL(m) in which the same number of scan points are disposed at different intervals.

More generally, the setting processor 231 may set the number of the scan points on the scan line SL(m1) and the number of the scan points on the scan line SL(m2) substantially equal to each other.

In the case of applying OCT motion contrast imaging to both the first region and the second region that are different in at least one of shape and size in order to improve the efficiency of panoramic OCT angiography, a scan point belonging to the first region may be used as the first scan point, and a scan point belonging to the second region as the second scan point. This makes it possible to carry out adjustment of the scan point dispositions on the scan lines belonging to mutually different regions. For example, the numbers of scan points on the scan lines belonging to mutually different regions may be made equal.

FIG. 5 shows a specific example. Here, the central part region 411 and the peripheral part region 412 which are the same as those shown in FIG. 4, are taken into account. The width (side length) of the central part region 411 is half the outer size (side length of the outer edge) of the peripheral part region 412. Each arrow indicates a scan line. Each of the black circles (black points, black dots) aligned along the scan lines indicates a scan point.

A scan mode applied to the central part region 411 is a raster scan that consists of a plurality of scan lines (B-scans) having the same length as the width of the central part region 411. A predetermined number (K) of scan points (A-scans) are aligned along each of the B-scans.

Regarding the peripheral part region 412, at least the region above the central part region 411 in FIG. 5 is scanned by a plurality of B-scans having the same length as the outer size of the peripheral part region 412. The number of A-scans belonging to each of the B-scans is the same as that for the central part region 411, which is K.

As mentioned above, the width of the central part region 411 is half the outer size of the peripheral part region 412. Therefore, the A-scan density in the central part region 411 is twice the A-scan density in the peripheral part region 412. Further, the A-scan intervals in the central part region 411 is half the scan intervals in the peripheral part region 412.

In this way, determining the same number of A-scans for scan lines having different lengths allows the repetitive imaging rate between the scan points to be constant, allows equivalent sensitivities in flow velocity to be obtained for different scan points, and allows relative flow velocities to be calculated.

It should be noted that while the scan points are arranged at equal intervals on a B-scan in the above example, scan point arrangements of embodiment examples are not limited to this. For example, scan points of some embodiment examples are arranged on a B-scan at unequal intervals. Here, the numbers of scan points disposed at unequal intervals are assumed to be constant (same).

The bias (unevenness) in the scan point density may be determined on the basis of the positions of eye fundus tissues, the positions of lesions, or the like. In some typical aspect examples, the scan point density at a site of interest may be set relatively high while the scan point density at other sites may be set relatively low. Here, the site of interest may be the macula, the optic nerve head, a blood vessel, or the like. In some other aspect examples, the scan point density at a lesion may be set relatively high while the scan point density at other sites may be set relatively low. This concludes the description of the example where the method (2) is employed.

Although the above illustrations have described the cases of using raster scans, applicable scan modes in embodiment examples are not limited to raster scans.

For example, in the case of being capable of setting a plurality of scan lines of the same length, the method described in the method (1) may be used.

On the other hand, in the case where a plurality of scan lines of the same length cannot be set, for example, the number of scan points (A-scans) belonging to each scan line may be made equal while setting a plurality of scan lines having different lengths. In other words, it is possible to perform adjustment of the scan point disposition (e.g., disposition intervals, density, etc.) on the basis of the differences in lengths of scan lines. Here is an example. In the case of using a concentric circle scan that consists of a plurality of circle scans with a common center and different diameters, scan point dispositions of the circle scans may be determined based on the ratios calculated from the lengths (circumferences) of the circle scans. Here, the numbers of scan points belonging to the circle scans are equal.

Some actions and some effects of the ophthalmic imaging apparatus 1 according to the present embodiment example will be described.

The ophthalmic imaging apparatus (1) according to the present embodiment example performs motion contrast imaging by applying optical coherence tomography (OCT) scanning to an eye. In addition, the ophthalmic imaging apparatus (1) includes the data acquiring unit, the image constructing unit, and the controller.

The data acquiring unit may be configured to repetitively apply an A-scan (to apply an A-scan several times, to apply multiple A-scans) to each of a plurality of scan points for motion contrast imaging. Here, the A-scan is a one dimensional scan along a depth direction. With such scanning, the data acquiring unit acquires a plurality of pieces of time-course data respectively corresponding to the plurality of scan points. In the aspect examples described above, the data acquiring unit includes the OCT unit 100 and elements of the fundus camera unit 2 that constitute the measurement arm such as the retroreflector 41, the OCT focusing lens 43, the optical scanner 44, the objective lens 22, etc.

The image constructing unit may be configured to construct a motion contrast image from the plurality of pieces of time-course data acquired by the data acquiring unit. In the aspect examples described above, the image constructing unit includes the image constructing unit 220.

The data acquiring unit may be configured to acquire the first time-course data by applying repetitive A-scan to the first scan point of the plurality of scan points. Further, the data acquiring unit may be configured to acquire the second time-course data by applying repetitive A-scan to the second scan point of the plurality of scan points. Here, the second scan point is different from the first scan point.

The controller may be configured to control the data acquiring unit in such a way that the data acquisition time intervals of the first time-course data and the data acquisition time intervals of the second time-course data become substantially equal to each other. In the aspect examples described above, the controller includes the main controller 211.

The image constructing unit may be configured to construct a one dimensional motion contrast image corresponding to the first scan point from the first time-course data, and construct a one dimensional motion contrast image corresponding to the second scan point from the second time-course data. Similarly, the image constructing unit may be configured to construct a plurality of one dimensional motion contrast images respectively corresponding to the plurality of scan points, from the plurality of pieces of time-course data acquired through the repetitive A-scan applied to individual scan points. From the plurality of one dimensional motion contrast images respectively corresponding to the plurality of scan points obtained in this manner, the image constructing unit may construct any of a two dimensional motion contrast image, a three dimensional motion contrast image (e.g., stack data, volume data), a rendered front image, and like images.

According to such an embodiment example, the time intervals at which multiple A-scans are applied (A-scan application rate) to the first scan point and the A-scan application rate to the second scan point can be made substantially equal to each other.

It should be noted that some embodiment examples may be configured to coincide not only the A-scan application rates for the two points of the first scan point and the second scan point with each other, but also a part or all of the A-scan application rates for the plurality of scan points with each other.

Further, scan modes to which the configuration according to the present embodiment example can be applied are not limited to raster scans, and may be any kinds of scan modes such as concentric circle scans described above, for example.

Such configuration examples allow the flow velocity sensitivity to be constant as well as the relative flow velocity to be calculated.

In addition, in the case where panoramic imaging is combined in order to widen the imaging area of OCT angiography, the repetitive imaging rates for a plurality of regions can be coincided with each other even when the sizes, the shapes, and/or other morphology of the plurality of regions are made uneven (diverse, various) in order to improve the efficiency of imaging.

In order to coincide the repetitive imaging rates (the A-scan application rates), any of the configurations illustrated below may be employed.

In some embodiment examples, it is supposed that the first route is defined to be a route of the movement of an A-scan application position in a direction perpendicular to the depth direction, between an A-scan application to the first scan point and the next A-scan application to the first scan point (during the time period from an A-scan application to the first scan point to the next A-scan application to the first scan point). Similarly, it is supposed that the second route is defined to be a route of the movement of an A-scan application position in a direction perpendicular to the depth direction, between an A-scan application to the second scan point and the next A-scan application to the second scan point (during the time period from an A-scan application to the second scan point to the next A-scan application to the second scan point). The ophthalmic imaging apparatus according to some embodiment examples may further include the first setting processor configured to set the first route and the second route. The controller may control the data acquiring unit based on the first route and the second route set by the first setting processor. In the aspect examples described above, the first setting processor includes the setting processor 231.

In some embodiment examples, the first setting processor may be configured to set the first route and the second route in such a manner that the length of the first route (the first route length) and the length of the second route (the second route length) are substantially equal to each other.

In addition to this, the first setting processor may be configured to set the scan point intervals of the first route and the scan point intervals of the second route substantially equal to each other.

In the case where repetitive scanning for motion contrast imaging is performed using a single scan line as a unit, the first scan point may be located on the first scan line and the second scan point may be located on the second scan line. Further, the first route may be the first scan line and the second route may be the second scan line. The controller may control the data acquiring unit so as to repeat an OCT scan along the first scan line a predetermined number of times consecutively and repeat an OCT scan along the second scan line a predetermined number of times consecutively.

Note that as described in the aspect examples described above, it is also possible to conduct repetitive scanning in motion contrast imaging by performing the same or similar processing in which a scan line group that consists of two or more scan lines is regarded as a unit.

In the case of applying panoramic OCT angiography to a plurality of regions having different morphologies from each other, the data acquiring unit may be configured to apply motion contrast imaging to both the first region and the second region that are different in at least one of their shapes and sizes. If this is the case, the first scan point may be located in the first region and the second scan point may be located in the second region.

The ophthalmic imaging apparatus according to some embodiment examples may further include the second setting processor. Note that as described above, the first route is the moving route of the A-scan application position in the direction perpendicular to the depth direction between an A-scan application to the first scan point and the next A-scan application to the first scan point. In a similar manner, the second route is the moving route of the A-scan application position in the direction perpendicular to the depth direction between an A-scan application to the second scan point and the next A-scan application to the second scan point. The second setting processor is configured to set (determine) a disposition of scan points on the first route (the first disposition) and a disposition of scan points on the second route (the second disposition). The controller may control the data acquiring unit based on the first disposition and the second disposition determined by the second setting processor.

In some embodiment examples, the second setting processor may be configured to set scan point intervals of the first route and scan point intervals of the second route such that the scan point intervals of the first route and the scan point intervals of the second route are different from each other. For example, the second setting processor may be configured to set scan point density of the first route and scan point density of the second route in such a manner that the values of the scan point density for the first and second routes are different from each other.

In addition to this, the second setting processor may be configured to set the length of the first route (the first route length) and the length of the second route (the second route length) such that the values of the first and second route lengths are different from each other.

Further, in some embodiment examples, the second setting processor may be configured to set the scan points on the first route and the scan points on the second route such that the number of the scan points on the first route and the number of the scan points on the second route are substantially equal to each other.

In the case of conducting repetitive scanning in motion contrast imaging in units of a single scan line, the first scan point may be located on the first scan line and the second scan point may be located on the second scan line. Further, the first route may be the first scan line and the second route may be the second scan line. The controller may execute control of the data acquiring unit so as to repeat an OCT scan along the first scan line a predetermined number of times consecutively and repeat an OCT scan along the second scan line a predetermined number of times consecutively.

Note that as described in the aspect examples described above, it is also possible to conduct repetitive scanning in motion contrast imaging by performing the same or similar processing in which a scan line group that consists of two or more scan lines is regarded as a unit.

In the case of applying panoramic OCT angiography to a plurality of regions of different morphologies from each other, the data acquiring unit may be configured to apply motion contrast imaging to both the first region and the second region that are different in at least one of the shapes and the sizes. If this is the case, the first scan point is a scan point located in the first region, and the second scan point is a scan point located in the second region.

A controlling method of an ophthalmic imaging apparatus according to some embodiment examples is a method of controlling the ophthalmic imaging apparatus that is capable of performing motion contrast imaging by applying optical coherence tomography (OCT) scanning to a subject's eye. The method of controlling the ophthalmic imaging apparatus includes the data acquiring step, the controlling step, and the image constructing step.

The data acquiring step includes a process of acquiring a plurality of pieces of time-course data respectively corresponding to a plurality of scan points for motion contrast imaging, by repetitively applying an A-scan to each of the plurality of scan points. Here, the A-scan is a one dimensional scan along the depth direction.

The controlling step may be executed in parallel with the data acquiring step. The controlling step includes a step of executing control for causing the data acquisition time intervals of the first time-course data corresponding to the first scan point of the plurality of scan points and the data acquisition time intervals of the second time-course data corresponding to the second scan point to become substantially equal to each other.

The image constructing step includes a step of constructing a motion contrast image from the plurality of pieces of time-course data acquired by the data acquiring step.

It is possible to create a computer program configured to cause a computer to execute the controlling method of the ophthalmic imaging apparatus of some embodiment examples. Further, it is possible to create a computer-readable non-transitory recording medium that stores the program of some embodiment examples. The non-transitory recording medium may have any form, and examples thereof include a magnetic disk, an optical disk, a magneto-optical disk, a semiconductor memory, and the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic imaging apparatus that performs motion contrast imaging by applying optical coherence tomography (OCT) scanning to an eye, comprising:
    a data acquiring unit including an optical scanner configured to acquire a plurality of pieces of time-course data respectively corresponding to a plurality of scan points of an imaging area by repetitively applying an A-scan to each of the plurality of scan points, the A-scan being a one dimensional scan along a depth direction;
    processing circuitry configured as an image constructing unit to construct a motion contrast image from the plurality of pieces of time-course data acquired by the data acquiring unit; and
    the processing circuitry is further configured as a controller to control the data acquiring unit such that data acquisition time intervals of first time-course data corresponding to a first scan point of the plurality of scan points and data acquisition time intervals of second time-course data corresponding to a second scan point become equal to each other, wherein the first scan point of the plurality of scan points is in a different position of the imaging area than the second scan point of the plurality of scan points,
    the ophthalmic imaging apparatus further comprising:
    a second setting processor configured to set a first disposition and a second disposition, the first disposition being a disposition of scan points on a first route that is a moving route of an A-scan application position in a direction perpendicular to the depth direction between an A-scan application to the first scan point and a next A-scan application to the first scan point, and the second disposition being a disposition of scan points on a second route that is a moving route of an A-scan application position in a direction perpendicular to the depth direction between an A-scan application to the second scan point and a next A-scan application to the second scan point, wherein
    the controller controls the data acquiring unit based on the first disposition and the second disposition set by the second setting processor,
    the second setting processor sets scan point intervals of the first route and scan point intervals of the second route different from each other, and
    the second setting processor sets a first route length that is a length of the first route and a second route length that is a length of the second route different from each other.

2. The ophthalmic imaging apparatus of claim 1, further comprising a first setting processor configured to set a first route and a second route, the first route being a moving route of an A-scan application position in a direction perpendicular to the depth direction between an A-scan application to the first scan point and a next A-scan application to the first scan point, and the second route being a moving route of an A-scan application position in a direction perpendicular to the depth direction between an A-scan application to the second scan point and a next A-scan application to the second scan point, wherein
    the controller controls the data acquiring unit based on the first route and the second route set by the first setting processor.

3. The ophthalmic imaging apparatus of claim 2, wherein the first setting processor sets the first route and the second route such that a first route length that is a length of the first route and a second route length that is a length of the second route are equal to each other.

4. The ophthalmic imaging apparatus of claim 3, wherein the first setting processor sets scan point intervals of the first route and scan point intervals of the second route equal to each other.

5. The ophthalmic imaging apparatus of claim 2, wherein
    the first scan point is located on a first scan line and the second scan point is located on a second scan line,
    the first route is the first scan line and the second route is the second scan line, and
    the controller controls the data acquiring unit to repeat an OCT scan along the first scan line predetermined number of times consecutively and repeat an OCT scan along the second scan line predetermined number of times consecutively.

6. The ophthalmic imaging apparatus of claim 2, wherein
    the data acquiring unit applies motion contrast imaging to both a first region and a second region that are different in at least one of a shape and a size, and
    the first scan point is located in the first region and the second scan point is located in the second region.

7. The ophthalmic imaging apparatus of claim 1, wherein the second setting processor sets a number of the scan points on the first route and a number of the scan points on the second route equal to each other.

8. The ophthalmic imaging apparatus of claim 1, wherein
    the first scan point is located on a first scan line and the second scan point is located on a second scan line,
    the first route is the first scan line and the second route is the second scan line, and
    the controller controls the data acquiring unit to repeat an OCT scan along the first scan line predetermined number of times consecutively and repeat an OCT scan along the second scan line predetermined number of times consecutively.

9. The ophthalmic imaging apparatus of claim 1, wherein the data acquiring unit applies motion contrast imaging to both a first region and a second region that are different in at least one of a shape and a size, and
the first scan point is located in the first region and the second scan point is located in the second region.

10. A method of controlling an ophthalmic imaging apparatus that performs motion contrast imaging by applying optical coherence tomography (OCT) scanning to an eye, comprising:
a data acquiring step of acquiring a plurality of pieces of time-course data respectively corresponding to a plurality of scan points of an imaging area by repetitively applying an A-scan to each of the plurality of scan points, the A-scan being a one dimensional scan along a depth direction;
a controlling step of executing, in parallel with the data acquiring step, control for causing data acquisition time intervals of first time-course data corresponding to a first scan point of the plurality of scan points and data acquisition time intervals of second time-course data corresponding to a second scan point to become equal to each other, wherein the first scan point of the plurality of scan points is in a different position of the imaging area than the second scan point of the plurality of scan points;
an image constructing step of constructing a motion contrast image from the plurality of pieces of time-course data acquired by the data acquiring step;
setting a first disposition and a second disposition, the first disposition being a disposition of scan points on a first route that is a moving route of an A-scan application position in a direction perpendicular to the depth direction between an A-scan application to the first scan point and a next A-scan application to the first scan point, and the second disposition being a disposition of scan points on a second route that is a moving route of an A-scan application position in a direction perpendicular to the depth direction between an A-scan application to the second scan point and a next A-scan application to the second scan point;
controlling the data acquiring step based on the first disposition and the second disposition;
setting scan point intervals of the first route and scan point intervals of the second route different from each other; and
setting a first route length that is a length of the first route and a second route length that is a length of the second route different from each other.

11. A computer-readable non-transitory recording medium that records a program causing a computer to execute the method of claim 10.

12. An ophthalmic imaging apparatus that performs motion contrast imaging by applying optical coherence tomography (OCT) scanning to an eye, comprising:
a data acquiring unit including an interface circuit configured to acquire, from an optical scanner, a plurality of pieces of time-course data respectively corresponding to a plurality of scan points of an imaging area by repetitively applying an A-scan to each of the plurality of scan points, the A-scan being a one dimensional scan along a depth direction;
processing circuitry configured as an image constructing unit to construct a motion contrast image from the plurality of pieces of time-course data acquired by the data acquiring unit; and
the processing circuitry is further configured as a controller to control the data acquiring unit such that data acquisition time intervals of first time-course data corresponding to a first scan point of the plurality of scan points and data acquisition time intervals of second time-course data corresponding to a second scan point become equal to each other, wherein the first scan point of the plurality of scan points is in a different position of the imaging area than the second scan point of the plurality of scan points,
the ophthalmic imaging apparatus further comprising:
a second setting processor configured to set a first disposition and a second disposition, the first disposition being a disposition of scan points on a first route that is a moving route of an A-scan application position in a direction perpendicular to the depth direction between an A-scan application to the first scan point and a next A-scan application to the first scan point, and the second disposition being a disposition of scan points on a second route that is a moving route of an A-scan application position in a direction perpendicular to the depth direction between an A-scan application to the second scan point and a next A-scan application to the second scan point, wherein
the controller controls the data acquiring unit based on the first disposition and the second disposition set by the second setting processor,
the second setting processor sets scan point intervals of the first route and scan point intervals of the second route different from each other, and
the second setting processor sets a first route length that is a length of the first route and a second route length that is a length of the second route different from each other.

* * * * *